US008992956B2

(12) United States Patent
Kwon et al.

(10) Patent No.: US 8,992,956 B2
(45) Date of Patent: Mar. 31, 2015

(54) COSMETIC COMPOSITION STABILIZED HIGHER OILY PART

(75) Inventors: Lee Kyoung Kwon, Yongin-si (KR); Go Un Han, Seoul (KR); Jun Oh Kim, Yongin-si (KR); Jeong Cheol Ha, Yongin-si (KR); Youn Joon Kim, Seoul (KR); Sang Hoon Han, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 301 days.

(21) Appl. No.: 13/512,204

(22) PCT Filed: Nov. 26, 2010

(86) PCT No.: PCT/KR2010/008421
§ 371 (c)(1),
(2), (4) Date: May 25, 2012

(87) PCT Pub. No.: WO2011/065771
PCT Pub. Date: Jun. 3, 2011

(65) Prior Publication Data
US 2012/0277313 A1     Nov. 1, 2012

(30) Foreign Application Priority Data
Nov. 27, 2009   (KR) .......................... 10-2009-0115509

(51) Int. Cl.
*A61K 8/02* (2006.01)
*A61K 8/06* (2006.01)
*A61Q 19/00* (2006.01)

(52) U.S. Cl.
CPC ................ *A61K 8/066* (2013.01); *A61Q 19/00* (2013.01)
USPC ........................................................ 424/401

(58) Field of Classification Search
None
See application file for complete search history.

(56) References Cited

U.S. PATENT DOCUMENTS

| 5,750,124 A | 5/1998 | Gohla et al. |
|---|---|---|
| 2004/0010078 A1 | 1/2004 | Nagahama et al. |
| 2009/0182060 A1 | 7/2009 | Nishioka et al. |
| 2012/0269752 A1* | 10/2012 | Ozee et al. ...................... 424/63 |

FOREIGN PATENT DOCUMENTS

KR   10-2003-0049558 A   6/2003

OTHER PUBLICATIONS

International Search Report for PCT/KR2010/008421, mailed Aug. 31, 2011.
Written Opinion of the International Searching Authority for PCT/KR2010/008421, mailed Aug. 31, 2011.

* cited by examiner

*Primary Examiner* — Carlos Azpuru
*Assistant Examiner* — Casey Hagopian
(74) *Attorney, Agent, or Firm* — Nixon & Vanderhye P.C.

(57) ABSTRACT

The present invention relates to a cosmetic composition having a high content of a stable oil phase, and more particularly to a cosmetic composition, which combines advantages of spreadability and softness of an oil-in-water type with emollient effect and water resistance of a water-in-oil type as a resulting of stabilizing, based on the total weight of the composition, 30-56 wt % of an oily component by multiple emulsification of W/O/W, and which provides skin moisturizing and softening effects by a large amount of oil components, and also which allows irritations caused by active ingredients to be relieved by a high content of the oily component.

10 Claims, 2 Drawing Sheets

US 8,992,956 B2

1

COSMETIC COMPOSITION STABILIZED HIGHER OILY PART

This application is the U.S. national phase of International Application No. PCT/KR 2010/008421, filed 26 Nov. 2010, which designated the U.S. and claims priority to Korea Application No. 10-2009-0115509, filed 27 Nov. 2009, the entire contents of each of which are hereby incorporated by reference.

TECHNICAL FIELD

The present invention relates to a cosmetic composition having a high content of a stable oil phase, and more particularly to a cosmetic composition, which combines advantages of spreadability and softness of an oil-in-water type (hereinafter also referred to as an "O/W type") with emollient effect and water resistance of a water-in-oil type (hereinafter also referred to as an "O/W type") as a resulting of stabilizing, based on the total weight of the composition, 30-56 wt % of an oily component by multiple emulsification of water/oil/water (hereinafter also referred to as "W/O/W type"), and which provides skin moisturizing and softening effects by a large amount of oily component, and also which irritations caused by active ingredients to be relieved by a high content of oily component.

BACKGROUND ART

In order to protect and keep the skin healthy, a variety of emulsion-type cosmetics, such as cream or lotion, have been used. Such cosmetic should allow the useful components contained therein to sufficiently exhibit their effects, should have a good sensory feel, and should be stable for a period ranging from opening of the package of the products to final use. Also, in order to provide long lasting moisturization and softness to the skin, efforts to incorporate a large amount of oil phase components have been made, and studies on O/W and W/O emulsion-type cosmetics have been conducted. Generally, cosmetic cream based on an O/W emulsion shows good spreadability, but is slightly inferior to W/O-type emulsion cosmetics with respect to emollient effects or water resistance, and cosmetic formulations having a high oil content are mostly glossy massage formulations showing fast phase transition and gloss. Also, W/O-type emulsion cosmetics disadvantageously have poor spreadability, do not give a fresh feel, unlike O/W-type emulsion cosmetics, and show a sticky and stuff feel, because they have a high oil content. In an attempt to solve such problems, studies on W/O/W multiple emulsion cosmetics combining the advantages of W/O-type emulsion cosmetics and O/W-type emulsion cosmetics have been actively conducted. However, because these W/O/W multiple emulsion cosmetics have a structure in which the inner water phase and the outer water phase are separated from each other by the thin oil film, the oil film can be broken due to an osmotic pressure phenomenon caused by the difference in electrolytic concentration between the outer water phase and the inner water phase, so that the water of the inner water phase can move, whereby they can lose their functions. Thus, the W/O/W multiple emulsion cosmetics have limitations in ensuring stability. In addition, it is more difficult to ensure the stability of the W/O/W emulsion cosmetics while they have an oil content of more than 30%. In an attempt to provide a cosmetic composition having a high content of a stable oil phase, the present invention has been devised in which a high content of an oil phase is stabilized by stabilizing a large amount of oil in an inner phase of W/O and

2 adding the inner phase having the stabilized oil phase to an outer phase. Also, functional cosmetics have appeared in the cosmetic markets, and customers have wanted highly functional and effective products. Under such circumstances, it has become to incorporate highly effective active ingredients into cosmetic formulations so as to have the highest possible safety, and whether the cosmetic formulations irritate the skin has been examined by skin safety tests. However, some patients complain of irritations such as tingling or burning feelings, and for this reason, efforts have been made to overcome such shortcomings. In some cases, active ingredients are encapsulated to regulate their penetration into the skin, thereby reducing the irritation thereof. However, in general cases, active ingredients are formulated with moisturizers and emollients for keeping the skin healthy, such that they can act on the skin without irritation. Namely, it is necessary but difficult to develop cosmetic compositions which have a stabilized oil phase in order to reduce irritation caused by active ingredients. Technical efforts to minimize this limitation have been made in the cosmetic field and related fields.

DISCLOSURE OF INVENTION

Technical Problem

Accordingly, the present inventors have prepared a cosmetic composition having a high content of a stable oil phase, the composition comprising a W/O formulation and an O/W phase as an outer phase, wherein the W/O formulation contains, based on the total weight of the W/O formulation, 1-8 wt % of a silicone-based emulsifier and a PEG-containing dipolyhydroxyalkylate-based emulsifier, 2.5-8 wt % of a hectorite-based oil thickener and a dextrin alkylate-based oil thickener, 0.1-5 wt % of a salt, and 20-45 wt % of a polar oil, and the outer phase contains 0.2-2 wt % of gum, and the present inventors have found that the cosmetic composition provides skin moisturizing and softening effects by a large amount of oily component, and which allows irritations caused by active ingredients to be relived by a high content of oily component, thereby completing the present invention.

It is, therefore, an object of the present invention to provide a cosmetic composition having a high content of a stable oil phase, the composition combining advantages of spreadability and softness of an O/W type and emollient effect and resistance of a W/O type as a result of stabilizing the high-oil-content phase of W/O/W by multiple emulsification by water/oil/water.

Solution to Problem

To achieve the above object, the present invention provides a cosmetic composition having a high content of a stable oil phase and being a W/O/W emulsion-type composition obtained by stabilizing, based on the total weight of the composition, 30-56 wt % of an oily component, the composition comprising a W/O formulation and an O/W phase as an outer phase, wherein the W/O formulation contains, based on the total weight of the W/O formulation, 1-8 wt % of a silicone-based emulsifier and a PEG-containing dipolyhydroxyalkylate-based emulsifier, 2.5-8 wt % of a hectorite-based oil thickener and a dextrin alkylate-based oil thickener, 0.1-5 wt % of a salt, and 20-45 wt % of a polar oil, and the outer phase contains 0.2-2 wt % of gum based on the total weight of the composition.

Advantageous Effects of Invention

The inventive cosmetic composition having a high content of a stable oil phase combines advantages of spreadability and softness of an oil-in-water type with emollient effect and water resistance of a water-in-oil type as a resulting of stabilizing, based on the total weight of the composition, 30-56 wt % of an oily component by multiple emulsification by W/O/W, and provides skin moisturizing and softening effects by a large amount of an oily component, and also allows irritations caused by active ingredients to be relieved by a high content of an oily component.

BEST MODE FOR CARRYING OUT THE INVENTION

Figure 1:
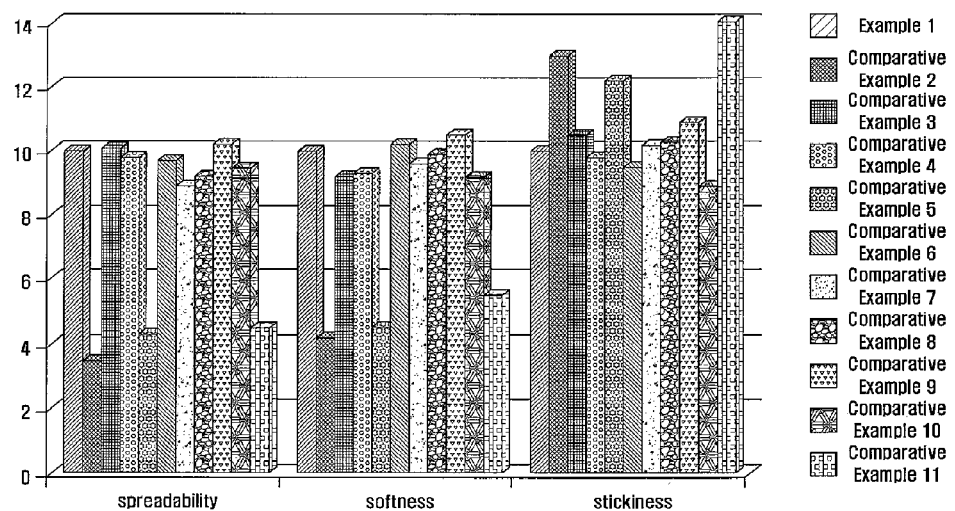
FIG. 1 shows the results of sensory evaluation for the spreadability, softness and stickiness of products of Example 1 and Comparative Examples 2 to 11 on the skin.

The present invention provides a cosmetic composition having a high content of a stable oil phase and being a W/O/W emulsion-type composition obtained by stabilizing, based on the total weight of the composition, 30-56 wt % of an oily component, the composition comprising a W/O formulation and an O/W phase as an outer phase, wherein the W/O formulation contains, based on the total weight of the W/O formulation, 1-8 wt % of a silicone-based emulsifier and a PEG-containing dipolyhydroxyalkylate-based emulsifier, 2.5-8 wt % of a hectorite-based oil thickener and a dextrin alkylate-based oil thickener, 0.1-5 wt % of a salt, and 20-45 wt % of a polar oil, and the outer phase contains 0.2-2 wt % of gum based on the total weight of the composition.

Hereinafter, the present invention will be described in further detail.

The present invention is a cosmetic composition which provides the advantages of W/O/W and the skin moisturizing and softening effects by a large amount of oil and relieves irritations caused by active ingredients.

As used herein, the term "silicone-based emulsifier in the W/O formulation" refers to an emulsifier which contains ethylene oxide or propylene oxide in dimethicone by alkoxylation or further contains polyglycerine or an alkyl chain (12-18 carbon atoms). Examples of the silicone-based emulsifier that may be used in the present invention include cetyl dimethicone copolyol, PEG-10 dimethicone, PEG-7 dimethicone, lauryl PEG-9 polydimethylsiloxyethyl dimethicone, lauryl polyglyceryl-3 polydimethylsiloxyethyl dimethicone, dimethicone PEG-10.15 crosspolymer/cyclosiloxane, dimethicone polyglycerine-3 crosspolymer/dimethicone, and cyclosiloxane/PEG.PPG-19.19 dimethicone.

The PEG-containing dipolyhydroxyalkylate-based emulsifier (represented by the following 1) of the W/O formulation is an emulsifier obtained by polymerizing dipolyhydroxy higher fatty acid with ethylene oxide. Examples of the dipolyhydroxy higher fatty acid include myristic acid, palmitic acid and stearic acid. Examples of the PEG-containing dipolyhydroxyalkylate-based emulsifier that may be used in the present invention include PEG-30 dipolyhydroxystearate, PEG-20 dipolyhydroxymyristate and PEG-40 dipolyhydroxypalmitate.

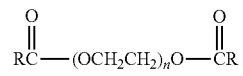

[Formula 1]

wherein R represents the alkyl group of dipolyhydoxy higher fatty acid, and n is a positive integer.

When the silicone-based emulsifier is used together with the PEG-containing dipolyhydroxyalkylate-based emulsifier, the stability of W/O is more increased compared to when the silicone-based emulsifier is used alone. The silicone-based emulsifier and the PEG-containing dipolyhydroxyalkylate-based emulsifier are contained in an amount of 1-8 wt % based on the total weight of the W/O formulation. If the content of the emulsifiers is less than 1 wt %, the W/O formulation itself is not stable, and if it is more than 8 wt %, the hard and sticky feel of the W/O formulation will be increased.

A hectorite-based oil thickener and a dextrin alkylate-based oil thickener are contained in the W/O formulation in order to increase the viscosity of the oil part, thereby stabilizing the high-oil-content phase of the W/O formulation. Examples of the hectorite-based oil thickener include stearalkonium hectorite, disteardimonium hectorite, and quaternium-18 hectorite. The dextrin alkylate-based oil thickener contains an alkyl chain in the dextrin, wherein the alkyl chain has 10-18 carbon atoms. Examples of the dextrin alkylate-based oil thickener that may be used in the present invention include dextrin palmitate, dextrin myristate, and dextrin stearate.

The hectorite-based oil thickener and the dextrin alkylate oil thickener are contained in an amount of 2.5-8 wt % based on the total weight of the W/O formulation. If the content of the thickener is less than 2.5 wt %, the thickening effect of the oil part will be insignificant such that the stability of the high oil phase cannot be maintained, and if the content is more than 8 wt %, the W/O formulation will a too high hardness, making it difficult to mix the oil phase with the outer phase, and will give an increased hard feel. Preferably, the hectorite-based oil thickener and the dextrin-based oil thickener are used in amounts of 0.5-3 wt % and 2-7.5 wt %, respectively. If the content of the hectorite-based oil thickener is less than 0.5 wt %, it cannot contribute to the thickening of the oil part, such that the stability of the oil part cannot be stabilized, and if the content is more than 3 wt %, the hardness of the W/O formulation will be increased, making it difficult to mix the W/O formulation with the outer phase. If the dextrin alkylate-based oil thickener is used in an amount of more than 2 wt %, it can thicken a large amount of oil to stabilize the oil, and it is highly compatible with silicone oil to assist in the stabilization of the silicone oil.

In order to control the osmotic pressure of the inner phase and the outer phase, the W/O formulation of the present invention contains an inorganic salt, an organic salt, or amino acid or its salt. Specific examples of the salt include sodium chloride and magnesium sulfate.

The salt is contained in an amount of 0.1-5 wt % based on the total weight of the W/O formulation. If the content of the salt is less than 0.1 wt %, it will be difficult to control the osmotic pressure, and if it is more than 5 wt %, the system becomes unstable due to the precipitation of the salt.

"Polar oil" which is used in the oil part of the W/O formulation of the present invention refers to an oil containing at least one carboxyl (COO—), ketone (CO—) or hydroxyl (OH) functional group. Examples of the polar oil include cetyl ethyl hexanoate (represented by the following formula 2), octyl dodecyl myristate, di-C12-13 alkyl malate, pentaerythrityl tetraisostearate, pentaerythrityl tetraethylhexanoate, diisostearyl malate, isopropyl palmitate, C12-15 alkyl benzoate, dicaprylic carbonate, dicaprylic ether, and 2-octyldodecanol.

[Formula 2]

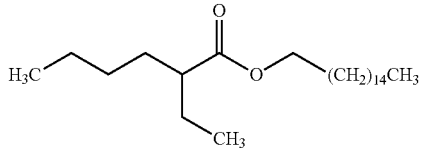

The polar oil is contained in an amount of 20-45 wt % based on the total weight of the W/O formulation. If it is used in an amount of less than 20 wt %, the oil-thickening effect can be reduced, and if it is used in an amount of more than 45 wt %, it will greatly increase the hardness of the W/O formulation, so that the W/O formulation will have a hard feel and will be difficult to mix with the outer phase.

The content of the oil phase in the W/O formulation of the present invention is 60-80 wt %. If the content of the oil phase is less than 60 wt %, the W/O/W composition will contain less than 30 wt % of the oily component, thus making it difficult to give moisturizing and softening effects, and if the content is more than 80 wt %, it will have poor stability when it is added to the W/O or the W/O/W, and the resulting composition will have a sticky feel.

Gum which is used in the outer phase O/W of the composition of the present invention is one or more selected from the group consisting of xanthan gum, carrageenans gum, guar gum, gellan gum and locust bean gum. The gum is insoluble in oil, assists in stability during mixing with the W/O formulation, is highly resistant to salt so as to assist in maintaining the viscosity of the outer phase, thereby assisting in the long-term stability of the W/O/W.

The gum in the present invention is contained in an amount of 0.2-2 wt % based on the total weight of the composition. If the content of the gum is less than 0.2 wt %, it cannot prevent the W/O formulation from being united with the outer phase, and the outer phase will have low stability leading to poor stability, and if the content is more than 2 wt %, it will disadvantageously increase a sticky and hard feel during use.

The W/O formulation prepared as described above is contained in an amount of 50-70 wt % based on the total weight of the W/O/W emulsion-type composition. If the W/O formulation is contained in an amount of less than 50 wt %, it cannot have a high oil phase content of more than 30 wt %, and thus will hardly give moisturizing and softening effects, and if it is contained in an amount of more than 70 wt %, the content of the W/O will be excessively large, making it difficult to maintain the formulation stability of the composition.

The cosmetic composition of the present invention may be formulated in the form of lotion, essence, cream or pack, and the formulation of the composition is not specifically limited.

Mode for the Invention

Hereinafter, the present invention will be described in further detail with reference to examples and comparative examples, but the scope of the present invention is not limited to these examples.

EXAMPLES 1 AND COMPARATIVE EXAMPLES 1 TO 17

According to the components and contents shown in Tables 1 to 7 below, a composition of Example 1 of the present invention and compositions of Comparative Examples 1 to 17 were prepared.

First, each of the W/O emulsion parts shown in Tables 1 and 2 was prepared, and then mixed with the components shown in Tables 3 to 5, thereby preparing W/O/W compositions. For this purpose, a water-phase part consisting of component Nos. 9 to 13 as shown in Tables 1 and 2 was placed in a separate container, dissolved by heating to 70° C., and then dispersed using a homogenizer, thereby a hydrophilic mixture. Meanwhile, an oil part consisting of component Nos. 1 to 8 was uniformly dispersed using a homogenizer and dissolved by heating to 75° C., and the above-described water phase part was added thereto and emulsified using a homogenizer at 70° C. for 4-5 minutes, thereby preparing a water-in-oil emulsion. The emulsion was degassed using a degassing unit and cooled to 35° C. using a cooling unit.

A water phase part consisting of component Nos. 2 to 4 as shown in Tables 3 to 5 (component Nos. 2 to 5 in Table 5) was dissolved well in a component No. 1 using a homogenizer, and then xanthan gum, a thickener and a pH adjusting agent were dispersed well therein, thereby preparing an outer phase. Then, the above-prepared W/O preparation of 35° C. was mixed with the outer phase using a homogenizer for 5 minutes, after which suitable amounts of a fragrance and a preservative were added thereto and mixed therewith using a homogenizer for 3 minutes. The resulting emulsion was degassed using a degassing unit, and the degassed emulsion was placed in a sealed container and then cooled to room temperature using a cooling unit.

In Table 6, an oil phase part consisting of component Nos. 1 to 12 was placed in a separate container, dissolved by heating to 70° C., and then dispersed using a homogenizer, thereby preparing an oleophilic mixture. Purified water of component No. 18 was added to a water phase part of components Nos. 13 to 15, and the solution was uniformly dispersed, dissolved by heating to 75° C. to form a hydrate, to which the above-prepared oleophilic mixture was then added. The mixture was emulsified using a homogenizer at 70° C. for 4-5 minutes. Then, a thickener and pH adjusting agent of component No. 17 and suitable amounts of a fragrance and preservative of component No. 18 were added thereto and mixed therewith using a homogenizer for 3 minutes, and then the resulting emulsion was cooled using a cooling unit to 30° C. and degassed using a degassing unit. The degassed emulsion was placed in a sealed container and then cooled using a cooling unit to room temperature.

In Table 7, a water phase part consisting of component Nos. 9-12 was placed in a separate container and dissolved by heating to 70° C. The solution was dispersed using a homogenizer to prepare a hydrophilic mixture. Meanwhile, an oil part of component Nos. 1 to 8 was uniformly dispersed using a homogenizer and dissolved by heating to 75° C., and the above-prepared water phase part mixture was added thereto. The resulting mixture was emulsified using a homogenizer at 70° C. for 4-5 minutes, thereby preparing water-in-oil emulsion. Then, suitable amounts of a fragrance and preservative were added thereto and mixed therewith using a homogenizer for 2 minutes. The resulting emulsion was degassed using a degassing unit and cooled using a cooling unit to room temperature.

TABLE 1

W/O emulsion part: Components and contents (wt %) of each composition

| NO | Components | Ex. WO1 | Ex. WO2 | Comp. Ex. WO1 | Comp. Ex. WO2 | Comp. Ex. WO3 |
|---|---|---|---|---|---|---|
| 1 | Cetyl ethyl hexanoate | 30.0 | 30.0 | 30.0 | 30.0 | 30.0 |
| 2 | Squalene | 15.0 | 20.0 | 15.0 | 15.0 | 15.0 |
| 3 | Dimethicone | 15.0 | 20.0 | 15.0 | 15.0 | 15.0 |
| 4 | Lauryl PEG-9 polydimethyl-siloxyethyl dimethicone | 2.0 | 2.0 | 0.5 | 3.9 | 2.0 |
| 5 | Cetyl dimethicone copolyol | 1.5 | 1.5 | 0.2 | 2.1 | 1.5 |
| 6 | PEG-30 dipolyhydroxystearate | 1.5 | 1.5 | 0.2 | 2.1 | 1.5 |
| 7 | Disteardimonium hectorite | 2.0 | 2.0 | 2.0 | 2.0 | 0.4 |
| 8 | Dextrin palmitate | 3.0 | 3.0 | 3.0 | 3.0 | 3.0 |
| 9 | Purified water | TO 100 | TO 100 | TO 100 | TO 100 | TO 100 |
| 10 | Sodium chloride | 1.0 | 1.0 | 1.0 | 1.0 | 1.0 |
| 11 | Glycerin | 5.0 | 5.0 | 5.0 | 5.0 | 5.0 |
| 12 | Butylene glycol | 5.0 | 5.0 | 5.0 | 5.0 | 5.0 |
| 13 | Preservative | q.s. | q.s. | q.s. | q.s. | q.s. |

TABLE 2

W/O emulsion part: Components and contents (wt %) of each composition

| NO | Components | Comp. Ex. WO4 | Comp. Ex. WO5 | Comp. Ex. WO6 | Comp. Ex. WO7 | Comp. Ex. WO8 | Comp. Ex. WO9 |
|---|---|---|---|---|---|---|---|
| 1 | Cetyl ethyl hexanoate | 30.0 | 30.0 | 30.0 | 30.0 | 19.0 | 31.0 |
| 2 | Squalene | 15.0 | 15.0 | 15.0 | 15.0 | 15.0 | 20.0 |
| 3 | Dimethicone | 15.0 | 15.0 | 15.0 | 15.0 | 15.0 | 20.0 |
| 4 | Lauryl PEG-9 polydimethyl-siloxyethyl dimethicone | 2.1 | 1.2 | 2.0 | 2.0 | 2.0 | 2.0 |
| 5 | Cetyl dimethicone copolyol | 1.5 | 1.5 | 1.5 | 1.5 | 1.5 | 1.5 |
| 6 | PEG-30 dipolyhydroxystearate | 1.5 | 1.5 | 1.5 | 1.5 | 1.5 | 1.5 |
| 7 | Disteardimonium hectorite | 2.0 | 3.1 | 2.0 | 2.0 | 2.0 | 2.0 |
| 8 | Dextrin palmitate | 1.9 | 5.0 | 3.0 | 3.0 | 3.0 | 3.0 |
| 9 | Purified water | TO 100 | TO 100 | TO 100 | TO 100 | TO 100 | TO 100 |
| 10 | Sodium chloride | 1.0 | 1.0 | 0.09 | 5.1 | 1.0 | 1.0 |
| 11 | Glycerin | 5.0 | 5.0 | 5.0 | 5.0 | 5.0 | 5.0 |
| 12 | Butylene glycol | 5.0 | 5.0 | 5.0 | 5.0 | 5.0 | 5.0 |
| 13 | Preservative | q.s. | q.s. | q.s. | q.s. | q.s. | q.s. |

TABLE 3

| NO | Components | Ex. 1 | Comp. Ex. 1 | Comp. Ex. 2 | Comp. Ex. 3 | Comp. Ex. 4 | Comp. Ex. 5 |
|---|---|---|---|---|---|---|---|
| 1 | Purified water | TO 100 | TO 100 | TO 100 | TO 100 | TO 100 | TO 100 |
| 2 | Disodium EDTA(EDTA) | 0.02 | 0.02 | 0.02 | 0.02 | 0.02 | 0.02 |
| 3 | Glycerin | 2.5 | 2.5 | 2.5 | 2.5 | 2.5 | 2.5 |
| 4 | Butylene glycol | 2.5 | 2.5 | 2.5 | 2.5 | 2.5 | 2.5 |
| 5 | Ex. WO1 | 60 | 0 | 0 | 0 | 0 | 0 |
| 6 | Comp. Ex. WO1 | 0 | 60 | 0 | 0 | 0 | 0 |
| 7 | Comp. Ex. WO2 | 0 | 0 | 60 | 0 | 0 | 0 |
| 8 | Comp. Ex. WO3 | 0 | 0 | 0 | 60 | 0 | 0 |
| 9 | Comp. Ex. WO4 | 0 | 0 | 0 | 0 | 60 | 0 |
| 10 | Comp. Ex. WO5 | 0 | 0 | 0 | 0 | 0 | 60 |
| 11 | Xanthan gum | 1 | 1 | 1 | 1 | 1 | 1 |
| 12 | Thickener, pH adjusting agent | q.s. | q.s. | q.s. | q.s. | q.s. | q.s. |
| 13 | Fragrance and preservative | q.s. | q.s. | q.s. | q.s. | q.s. | q.s. |

TABLE 4

| NO | Components | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
| 1 | Purified water | TO 100 | TO 100 | TO 100 | TO 100 | TO 100 | TO 100 |
| 2 | Disodium EDTA(EDTA) | 0.02 | 0.02 | 0.02 | 0.02 | 0.02 | 0.02 |
| 3 | Glycerin | 2.5 | 2.5 | 2.5 | 2.5 | 2.5 | 2.5 |

TABLE 4-continued

| NO | Components | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
| 4 | Butylene glycol | 2.5 | 2.5 | 2.5 | 2.5 | 2.5 | 2.5 |
| 5 | Ex. WO1 | 0 | 0 | 0 | 0 | 60 | 60 |
| 6 | Comp. Ex. WO6 | 60 | 0 | 0 | 0 | 0 | 0 |
| 7 | Comp. Ex. WO7 | 0 | 60 | 0 | 0 | 0 | 0 |
| 8 | Comp. Ex. WO8 | 0 | 0 | 60 | 0 | 0 | 0 |
| 9 | Comp. Ex. WO9 | 0 | 0 | 0 | 60 | 0 | 0 |
| 10 | Xanthan gum | 1 | 1 | 1 | 1 | 0.1 | 2.1 |
| 11 | Thickener, pH adjusting agent | q.s. | q.s. | q.s. | q.s. | q.s. | q.s. |
| 12 | Fragrance and Preservative | q.s. | q.s. | q.s. | q.s. | q.s. | q.s. |

TABLE 5

| NO | Components | Ex. 2 | Comp. Ex. 12 | Comp. Ex. 13 | Comp. Ex. 14 | Comp. Ex. 15 |
|---|---|---|---|---|---|---|
| 1 | Purified water | TO 100 | TO 100 | TO 100 | TO 100 | TO 100 |
| 2 | Disodium EDTA | 0.02 | 0.02 | 0.02 | 0.02 | 0.02 |
| 3 | Glycerin | 2.5 | 2.5 | 2.5 | 2.5 | 2.5 |
| 4 | Butylene glycol | 2.5 | 2.5 | 2.5 | 2.5 | 2.5 |
| 5 | Sallicylic acid | 5 | 0 | 0 | 0 | 5 |
| 6 | Ex. WO1 | 60 | 41 | 0 | 71 | 41 |
| 7 | Ex. WO2 | 0 | 0 | 71 | 0 | 0 |
| 8 | Xanthan gum | 1 | 1 | 1 | 1 | 1 |
| 9 | Thickener, pH adjusting agent | q.s. | q.s. | q.s. | q.s. | q.s. |
| 10 | Fragrance and Preservative | q.s. | q.s. | q.s. | q.s. | q.s. |

TABLE 6

| NO | Components | Comp. Ex. 16 |
|---|---|---|
| 1 | Stearic acid | 1 |
| 2 | Bees wax | 0.3 |
| 3 | Stearyl Alcohol | 1.6 |
| 4 | Hydrogenated oil | 0.5 |
| 5 | PEG-100 Stearate | 1.6 |
| 6 | Lipophilic glyceryl stearate | 2 |
| 7 | Glyceryl stearate SE | 1 |
| 8 | Sorbitan sesquioleate | 1 |
| 9 | Hydrogenated polyisobutene | 22 |
| 10 | Dimethicone | 1 |
| 11 | 2-Octyl dodecanol | 4 |
| 12 | Cyclomethicone | 6 |
| 13 | Purified water | to 100 |
| 14 | Disodium EDTA | 0.02 |
| 15 | Propylene glycol | 5 |
| 16 | Glycerin | 2 |
| 17 | Thickener, pH adjusting agent | q.s. |
| 18 | Fragrance and Preservative | q.s. |

TABLE 7

| NO | Components | Comp. Ex. 17 |
|---|---|---|
| 1 | Cetyl ethyl hexanoate | 20.5 |
| 2 | Squalene | 10.0 |
| 3 | Bees wax | 0.5 |
| 4 | Dimethicone | 5.0 |
| 5 | Lauryl PEG-9 polydimethylsiloxyethyl dimethicone | 2.0 |
| 6 | cetyl dimethicone copolyol | 1.5 |
| 7 | PEG-30 dipolyhydroxystearate | 1.5 |
| 8 | Disteardimonium hectorite | 1.0 |
| 9 | Purified water | TO 100 |
| 10 | Sodium chloride | 0.5 |
| 11 | Glycerin | 5.0 |
| 12 | Butylene glycol | 5.0 |
| 13 | Fragrance and Preservative | q.s. |

TEST EXAMPLE 1

Comparison of Formulation Stabilities of W/O Formulations According to the Contents of Surfactant, Oil Thickener, Salt and Oil and Formulation Stabilities of W/O/W Formulations According to the Content of Gum in Outer Phase The formulation stabilities of Example WO1 and Comparative Examples WO1 to WO9 according to the surfactant, oil thickener, salt and oil contents were comparatively evaluated by storing them in an incubator at 45° C. and measuring the phase separation time. Also, the W/O/W formulations of Example 1 and Comparative Examples 1 to 11, prepared by adding the W/O formulation to the O/W formulation, were evaluated by storing them in an incubator at 45° C. and measuring the phase separation time. The results of the evaluation are shown in Table 8 below.

The formulations of Example 1 and Comparative Examples 1 to 11 were subjected to sensory evaluation for spreadability, softness and stickiness. For this purpose, on twenty women in their thirties, the formulations of Example 1 and Comparative Examples 1 to 11 were applied to the face. Specifically, the formulation of Example 1 was applied to one cheek with rubbing, and each of the formulations of Comparative Examples was applied to the other cheek with rubbing, and then the spreadability and softness thereof were examined through questionnaire. Based on Example 1 taken as 10, Comparative Examples were rated on a score of 0 to 20, and the rated scores were averaged. The results of the evaluation are shown in Table 9 below and FIG. 1.

TABLE 8

| Experimental Example | Formulation stabilities |
| --- | --- |
| Ex. WO1 | Stable for 8 weeks at 45° C. |
| Comp. Ex. WO1 | Separated at room temperature |
| Comp. Ex. WO2 | Stable for 8 week at 45° C. |
| Comp. Ex. WO3 | Stable for 1 week at 45° C. |
| Comp. Ex. WO4 | Stable for 1 week at 45° C. |
| Comp. Ex. WO5 | Stable for 9 weeks at 45° C. |
| Comp. Ex. WO6 | Stable for 2 weeks at 45° C. |
| Comp. Ex. WO7 | Stable for 1 week at 45° C. |
| Comp. Ex. WO8 | Stable for 2 weeks at 45° C. |
| Comp. Ex. WO9 | Stable for 4 days at 45° C. |
| Ex. WO1 | Stable for 8 weeks at 45° C. |
| Ex. WO1 | Stable for 8 weeks at 45° C. |
| Ex. 1 | Stable at 20 weeks at 45° C. |
| Comp. Ex. 1 | No W/O mixture |
| Comp. Ex. 2 | Stable for 18 weeks at 45° C. |
| Comp. Ex. 3 | Stable for 2 weeks at 45° C. |
| Comp. Ex. 4 | Stable for 2 weeks at 45° C. |
| Comp. Ex. 5 | Stable for 21 weeks at 45° C. |
| Comp. Ex. 6 | Stable for 4 weeks at 45° C. |
| Comp. Ex. 7 | Stable for 2 weeks at 45° C. |
| Comp. Ex. 8 | Stable for 5 weeks at 45° C. |
| Comp. Ex. 9 | Stable for 1 week at 45° C. |
| Comp. Ex. 10 | Stable for 4 weeks at 45° C. |
| Comp. Ex. 11 | Stable for 22 weeks at 45° C. |

TABLE 9

| Experimental Example | Spreadability | Softness | Stickiness |
| --- | --- | --- | --- |
| Ex. 1 | 10 | 10 | 10 |
| Comp. Ex. 1 | No comparison | No comparison | No comparison |
| Comp. Ex. 2 | 3.5 | 4.2 | 13 |
| Comp. Ex. 3 | 10.1 | 9.2 | 10.5 |
| Comp. Ex. 4 | 9.8 | 9.3 | 9.9 |
| Comp. Ex. 5 | 4.3 | 4.5 | 12.2 |
| Comp. Ex. 6 | 9.7 | 10.2 | 9.5 |
| Comp. Ex. 7 | 8.9 | 9.6 | 10.2 |
| Comp. Ex. 8 | 9.2 | 9.9 | 10.3 |
| Comp. Ex. 9 | 10.2 | 10.5 | 10.9 |
| Comp. Ex. 10 | 9.5 | 9.2 | 8.9 |
| Comp. Ex. 11 | 4.5 | 5.5 | 14 |

As can be seen in Tables 8 and 9, Example WO1 was stable for 8 weeks at 45° C., and the W/O/W of Example 1, obtaind by adding the WO1 to the O/W, also had good stability.

In the csse of Comparative Example WO1 in which the PEG-containing dipolyhy-droxyalkylate-based emulsifier and the silicone-based emulsifier were used in an amount of less than 1 wt %, it was separated at room temperature, and thus it was imposible to make a multiple emulsion. In the case of Comparative Example WO2 in which the PEG-containing dipolyhydroxyalkylate-based emulsifier and the silicone-based emulsifier were used in an amount of more than 8 wt %, the W/O itself was stable for 8 weeks similar to Example WO1, and the stability of the W/O/W was also similar to Example 1, but the spreadability or softness thereof was reduced to ⅓ of Example 1, and the stickiness thereof was also increased by more than 30% compared to Example 1.

In the case of Comparative Example WO3 in which the hectorite-based oil thickener was used in an amount of less than 0.5 wt %, it was stable for about 1 week at 45° C., indicating a stability of 12.5% compared to Example WO1. The W/O/W formulaiton of Comparative Example 3 was also stable for about 1 week at 45° C., and thus the stability thereof was inferior to Example 1. Moreover, in the case of Comparartive Example WO4 in which the dextrin alkylate-based oil thcikener was used in an amount of less than 2wt %, it was stable for about 1 week at 45° C., indicating a stability of 12.5% compared to Example W01. In addition, the W/O/W formulation of Comparative Example 4 was stable for about 1 week at 45° C., and thus the stability thereof was inferior to Example 1.

Comparative Example WO5 and Comparative Example 5 in which the oil thickener was used in an amount of more than 8 wt % showed formulaiton stability similar to Example 1, but the spreadability and softness thereof were about 40% of Example 1, indicating a poor feel.

In the case of Comparative Example WO6 in which the salt was used in an amount of less thanb 0.1 wt %, the stability thereof was reduced to about 25% of Example WO1. Also, the stability of the W/O/W of Comparative Example 6, obtained by adding the WO6, was reduced to about 20% of Example 6. In the case of Comparative Example WO7 in which the salt was used in an amount of more than 5 wt %, the stability was reduced to about 12.5% of Example WO1, and the stability of the W/O/W of Compatative Example 7, obtained by adding the WO7, was reduced to about 10% of Example 1 due to the precipitation of the salt.

In the case of Comparative Example WO8 in which the polar oil was used in an amount of less than 20 wt %, the stability was reduced to about 25% of Example WO1, and the stability of Comparative Example 8 was also reduced to about 25% of Example 1.

In the case of Comparative Example WO9 in which the oil was contained in an amount of more than 80 wt %, it was stable for 4 days at 45° C., indicating a stability of about 7% compared to Example WO1, and the W/O/W containing the WO9 showed stability corresponding to about 5% of the stability of Example 1.

In the case of Comparative Example 10 in which the gum was contained in an amount of less than 0.1 wt %, the stability was reduced to about 20% of Example 1. Also, in the case of Comparative Example 11 in which the gum was used in an amount of more than 2.0wt %, the stability was similar to that of Example 1, but the spreadability and softness thereof were reduced to about 50% of Example 1, indicating a hard feel, and the stickiness thereof was increased by more than 40% compared to that of Example 1, indicating a poor feel.

TEST EXAMPLE 2

Measurement of Formulation Stability and Moisturizing Activity of W/O/W According to Content of Oily Component and the Content of W/O The formulation stabilities of Example 1 and Comparative Examples 12 to 14 were evaluated by storing them in an incubator at 45° C. and measuring the phase separation time. The results of the evaluation are shown in Table 10 below.

A skin moisturization test was conducted on 20 persons. The left and right sides of the lower arms were washed with soap, and then the skin was adapted to constant temperature and constant humidity conditions (20±2° C., relative humidity 40±2%). The skin softening effect was evaluated by the skin moisturization test as follows. On the left and right sides of the inner side of the lower arm, 6 rectangular test portions, each having an area of 4×3 cm$^2$, were selected. The capacitance of the skin surface was measured three times using a corneometer (CM825). Specifically, 24 μl (2 mg/cm$^2$) of each of the samples of Example 1 and Comparative Examples 12 to 14 was randomly applied to the selected test portions. 6 hours after the application, the capacitance of the skin surface was measured three times using a corneometer. Herein, the skin was adapted to constant temperature and constant humidity conditions.

The three measurements of the capacitance were averaged, and the average value was used as a water content. The initial water content before the application and the water content of the portion to which the sample was not applied were corrected, and the change in water content was calculated according to the following equation 1. Based on the calculation results, the moisturizing activity of the sample was determined. The results are shown in Table 10 below.

Change in water content (%)=|{[(Tdi−Td0)−(Ntdi−NTd0)]/[(Ntdi−NTd0)+Td0]}*100|     [Equation 1]

wherein Tdi=n$^{st}$ measurement value of sample-applied portion;

Td0=measurement value of sample-applied portion before application;

NTdi=n$^{st}$ measurement value of sample-non-applied portion; and

NTd0=measurement value of sample-non-applied portion before application.

TABLE 10

| Experimental Example | Formulation stabilities | Moisturizing activity |
|---|---|---|
| Ex. 1 | Stable for 20 weeks at 45° C. | 20 |
| Comp. Ex. 12 | Stable for 20 weeks at 45° C. | 12.9 |
| Comp. Ex. 13 | Stable for 2 weeks at 45° C. | 24.5 |
| Comp. Ex. 14 | Stable for 3 weeks at 45° C. | 21 |

Figure 2:
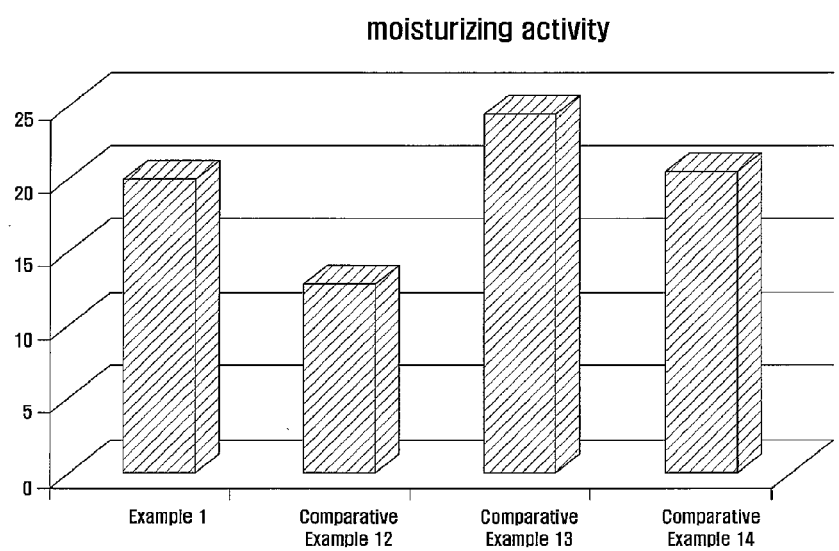
FIG. 2 shows the results of measuring the skin moisturizing activities of Example 1 and Comparative Examples 12 to 14.

As can be seen in Table 10 above and FIG. 2, when Example 1 containing 24 wt % of the oily component in the W/O/W formulaiton was compared with Comparative Example 12 containing 28.7 wt % of the oily component, Example 1 and Comparative Example 12 had similar stabilities, but the moisturizing activity of Comparative Example 12 containing less than 30 wt % of the oily component was reduced to about 64.5% of Example 1. Comparative Example 13 showed a moisturizing activity higher than that of Example 1 by about 22.5%, because it contained 56.8 wt % of the oily component, but the stability thereof was reduced to less than 10% of Example 1, because it contained more than 70 wt % of the W/O formulation. Comparative Example 14 showed moisturizing activity similar to Example 1, because it contained more than 49.7wt % of oily component, but the stability thereof was reduced to about 42% of Example 1, because it contained more than 70wt % of the W/O formulation.

TEST EXAMPLE 3

Comparison of Moisturizing Activity and Sensory Feel Between W/O/W Formulation and Conventional O/W and W/O Formulations Example 1 and comparative Examples 16 and 17 were subjected to sensory evaluation for spreadability, softness and stickiness. Herein, Example 1 and Comparative Examples 16 and 17 had the same oil phase content of 42 wt %, but Example 1 was a W/O/W formulation, Comparative Example 16 was a conventional O/W formulation, and Comparative Example 17 was a conventional W/O formulation. On twenty women in their thirties, the formulations of Example 1 and Comparative Examples 16 and 17 were applied to the face. Specifically, the formulation of Example 1 was applied to one cheek, and each of the formulations of Comparative Examples 16 and 17 was applied to the other cheek, and then the spreadability, softness and stickiness thereof were examined through questionnaire. Based on Example 1 taken as 10, Comparative Examples were rated on a score of 0 to 20, and the rated scores were averaged. A skin moisturization test was performed in the same manner as Test Example 2. The results of the evaluation are shown in Table 11 below and FIG. 3.

TABLE 11

| Experimental Example | Moisturizing activity | spreadability | Softness | Stickiness |
|---|---|---|---|---|
| Ex. 1 | 20 | 10 | 10 | 10 |
| Comp. Ex. 16 | 13.5 | 12.1 | 11.5 | 9.8 |
| Comp. Ex. 17 | 19.2 | 4.8 | 7.5 | 14.5 |

Figure 3:
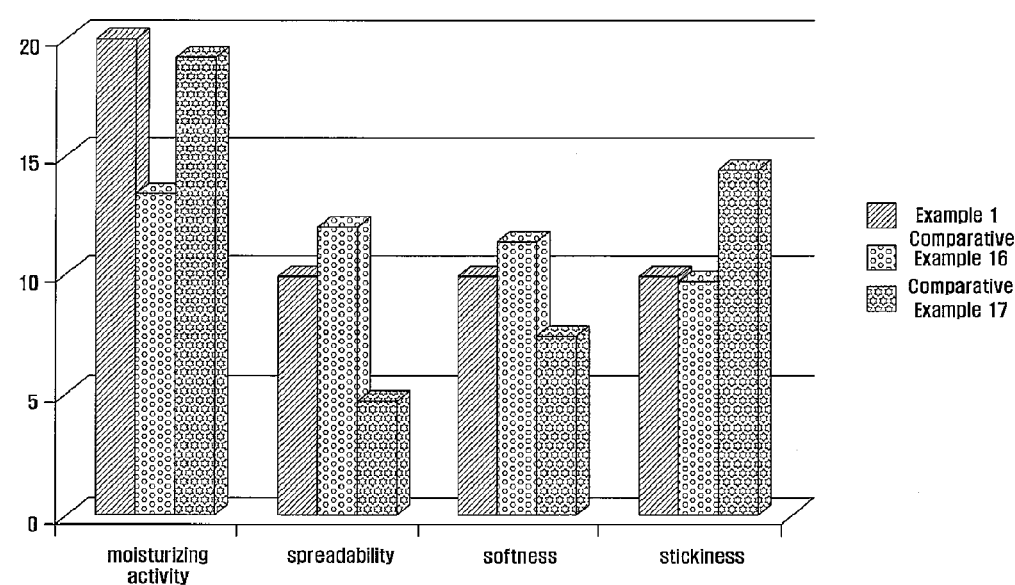
FIG. 3 shows the results of sensory evaluation for the spreadability, softness and stickiness of products of Example 1 and Comparative Examples 16 and 17 on the skin and the results of measuring the skin moisturizing activity of the products.

As can be seen in Table 11 above and FIG. 3, although Example 1 and Comparative Examples 16 and 17, the moisturizing activty of the W/O/W formulation of Example was reduced to about 67% of the O/W formulation of Comparative Example 16, and the W/O formulation of Comparative Example 17 showed moisturizing activity similar to Example 1. However, in the case of the W/O formulation of Comparative Example 17, the spreadability was reduced to less than 50% of Example 1, the softness was reduced to about 75%, and the stickiness was increased to more than 45%.

TEST EXAMPLE 4

Comparison of Irritations Caused by Active Ingredients According to High Oil-Phase Content of W/O/W Formulations An irritation test was performed on 20 persons. Both cheekbone portions of the face were washed with soap, and then the skin was adapted to constant temperature and constant humidity conditions (20±2° C., relative humidity 40±2%). 3 ml of each of Example 2 and Comparative Example 13 was randomly applied to both sides of the face, and was evaluated for irritations, including tingling, burning and itching feelings. Based on Example 2 taken as 10, Comparative Example 15 was rated on a score of 0 to 20, and the rated scores were averaged. The results of the evaluation are shown in Table 12.

TABLE 12

| | Tingling feeling | Burning feeling | Itching feeling |
|---|---|---|---|
| Ex. 2 | 10 | 10 | 10 |
| Comp. Ex. 15 | 16.4 | 15.6 | 10.5 |

Example 2 and Comparative Example 15 contained salicylic acid and alpha-hydroxyl acid as active ingredients, and Example 2 had an oil phase content of 42 wt %, and Comparative Example 17 had an oil phase content of 28.7 wt %. As can be seen in Table 12 above, the irritations (including tingling and burning) of Comparative Example 15 were more than 1.5 times than those of Example 2. This suggests that the composition of the present invention relieves irritation, because it has a high oil-phase content.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A cosmetic composition having a high content of a stable oil phase and being a W/O/W emulsion-type composition obtained by stabilizing, based on the total weight of the composition, 30-56 wt % of an oily component(s), the composition comprising a W/O emulsion part and an O/W phase as an outer phase, wherein the W/O emulsion part contains, based on the total weight of the W/O emulsion part, 1-8 wt % of a silicone-based emulsifier and a PEG-containing dipolyhydroxyalkylate-based emulsifier, 2.5-8 wt % of a hectorite-based oil thickener and a dextrin alkylate-based oil thickener, 0.1-5 wt % of a salt, and 20-45 wt % of a polar oil, and the O/W outer phase contains 0.2-2 wt % of gum based on the total weight of the composition,
wherein the polar oil is at least one selected from the group consisting of cetyl ethyl hexanoate, octyl dodecyl myristate, di-C12-13 alkyl malate, pentaerythrityl tetraisostearate, pentaerythrityl tetraethylhexanoate, diisostearyl malate, isopropyl palmitate, C12-15 alkyl benzoate, dicaprylic carbonate, dicaprylic ether, and 2-octyldodecanol.

2. The cosmetic composition of claim 1, wherein the composition comprises, based on the total weight of the composition, 50-70 wt % of a W/O emulsion part and 30-50 wt % of an O/W outer phase.

3. The cosmetic composition of claim 1, wherein the silicone-based emulsifier is at least one selected from the group consisting of cetyl dimethicone copolyol, PEG-10 dimethicone, PEG-7 dimethicone, lauryl PEG-9 polydimethylsiloxyethyl dimethicone, lauryl polyglyceryl-3 polydimethylsiloxyethyl dimethicone, dimethicone PEG-10·15 crosspolymer/cyclosiloxane, dimethicone polyglycerine-3 crosspolymer/dimethicone, and cyclosiloxane/PEG.PPG-19.19 dimethicone.

4. The cosmetic composition of claim 1, wherein the PEG-containing dipolyhydroxyalkylate-based emulsifier is at least one selected from the group consisting of PEG-30 dipolyhydroxystearate, PEG-20 dipolyhydroxymyristate and PEG-40 dipolyhydroxypalmitate.

5. The cosmetic composition of claim 1, wherein the hectorite-based oil thickener is at least one selected from the group consisting of stearalkonium hectorite, disteardimonium hectorite, and quaternium-18 hectorite.

6. The cosmetic composition of claim 1, wherein the dextrin alkylate-based oil thickener is at least one selected from the group consisting of dextrin palmitate, dextrin myristate, and dextrin stearate.

7. The cosmetic composition of claim 1, wherein the salt is either sodium chloride or magnesium sulfate.

8. The cosmetic composition of claim 1, wherein the polar oil is cetyl ethyl hexanoate.

9. The cosmetic composition of claim 1, wherein the W/O emulsion part contains, based on the total weight of the W/O emulsion part, 60-80 wt % of an oily components.

10. The cosmetic composition of claim 1, wherein the gum is at least one selected from the group consisting of xanthan gum, carrageenans gum, guar gum, gellan gum and locust bean gum.

* * * * *